United States Patent [19]
Müller et al.

[11] Patent Number: 5,817,659
[45] Date of Patent: Oct. 6, 1998

[54] STABLE CRYSTALLINE TETRAHYDROFOLIC ACID SALTS

[75] Inventors: Hans R. Müller, Schaffhausen; Martin Ulmann, Dachsen; Rudolf Moser, Schaffhausen; Thomas Ammann, Marthalen, all of Switzerland

[73] Assignee: Eprova AG, Switzerland

[21] Appl. No.: 744,952

[22] Filed: Nov. 7, 1996

[30] Foreign Application Priority Data

Nov. 7, 1995 [CH] Switzerland .......................... 03145/95

[51] Int. Cl.[6] .......................... A01N 43/58; C07D 475/00
[52] U.S. Cl. ............................................ 514/249; 544/258
[58] Field of Search .............................. 544/258; 514/249

[56] References Cited

U.S. PATENT DOCUMENTS 5,489,684  2/1996  Jequier et al. .......................... 544/258

*Primary Examiner*—Mukund J. Shah
*Assistant Examiner*—Tamthom T. Ngo
*Attorney, Agent, or Firm*—Millen, White, Zelano & Branigan, P.C.

[57] ABSTRACT

This invention relates to stable crystalline salts of (6R,S)-, (6S)- and (6R)-tetrahydrofolic acid, to methods of preparing these salts and to their use as an ingredient for the production of drugs and pharmaceutical preparations.

9 Claims, No Drawings

STABLE CRYSTALLINE TETRAHYDROFOLIC ACID SALTS

This invention relates to crystalline N-[4-[[2-amino-1,4,5,6,7,8-hexahydro-4-oxo-(6S)-, -(6R)- and -(6R,S)-pteridinyl)methyl]amino]benzoyl]-L-glutamic acid salts (hereinafter called tetrahydrofolic acid salts), to the use thereof, and to a method of preparing them.

Tetrahydrofolic acid derivatives contain two asymmetric centers. In this connection, due to the synthesis of these derivatives from folic acid, N-(pteroyl)-L-glutamic acid, the optically active C atom which is contained in the glutamic acid radical is present in the L-form, while the optically active C atom in position 6, which is usually formed by hydrogenation of the double bond in the 5,6-position of the pteroyl radical, is present in the racemic (6R,S)- form. Synthetic derivatives of tetrahydrofolic acid accordingly consist of a 1:1 mixture of 2 diastereoisomers.

As drugs, tetrahydrofolates are predominantly used as the calcium salt of 5-formyl-5,6,7,8-tetrahydrofolic acid (leucovorin) or of 5-methyl-5,6,7,8-tetrahydrofolic acid for the treatment of megaloblastic folic acid anaemia, as an antidote to increase the compatibility of folic acid antagonists, particularly of aminopterin and methotrexate in cancer therapy ("antifolate rescue"), for increasing the therapeutic effect of fluorinated pyrimidines and for the treatment of autoimmune diseases such as psoriasis and rheumatic arthritis, for increasing the compatibility of certain antiparasitic agents, for instance trimethoprim-sulphamethoxazole, and for reducing the toxicity of dideazatetrahydrofolates in chemotherapy. In the body, the individual tetrahydrofolic acid derivatives can be transformed into one another (folate cycle). Tetrahydrofolic acid plays a central part in such processes. Tetrahydrofolic acid is also employed as a basic substance for the preparation of diverse tetrahydrofolic acid derivatives.

Hitherto, the direct use of tetrahydrofolic acid salts as drugs or as a basic substance for the preparation of diverse tetrahydrofolic acid derivatives has failed, due to the difficulty of producing tetrahydrofolic acid salts with an acceptable purity for a pharmaceutical active ingredient, and due to the extreme instability of tetrahydrofolic acid, particularly its high susceptibility to oxidation [on this topic, see A. L. Fitzhugh, Pteridines $\underline{4}$ (4), 187–191 (1993)]. In this connection, it should be remarked that for the parenteral use of tetrahydrofolates, which is the one most frequently employed in the pharmaceutical field, an at least approximately neutral pH of the solution administered is a mandatory prerequisite. For this use, salts of tetrahydrofolates are therefore the preferred form of application. Various methods have been employed in order to overcome the instability of tetrahydrofolic acid, such as the exclusion of oxygen as completely as possible or the addition of antioxidants such as ascorbic acid. For a pharmaceutical use, however, the complete exclusion of oxygen is scarcely possible, and even then can only be achieved at very high cost, and the addition of antioxidants is likewise not always possible for pharmaceutical application. Accordingly, it has hitherto still not been possible to discover a commercially practicable method which is suitable for the preparation of tetrahydrofolic acid salts of high purity and adequate stability and which would thus make possible the pharmaceutical use of tetrahydrofolic acid salts.

Surprisingly, it has now been found that (6S)-, (6R)- or (6R,S)-tetrahydrofolic acid salts can be obtained in high purity and with excellent stability by crystallizing the corresponding salt of optically pure (6S)- or optically pure (6R)-, of enriched (6S)- or enriched (6R)-, or of (6R,S)-tetrahydrofolic acid also. The crystalline (6S)-, (6R)- and/or (6R,S)- tetrahydrofolic acid salts which are thus obtained are of practically unlimited stability in suitable form at room temperature. They are suitable as an ingredient or as a starting material for the production of forms of drugs, or as a starting material for the commercial production of other tetrahydrofolic acid derivatives of high purity.

The present invention accordingly relates to crystalline salts of (6R,S)-, (6S)- and (6R)-tetrahydrofolic acid. Alkaline earth salts, particularly the calcium or magnesium salt, are preferably used as salts of tetrahydrofolic acid for crystallization.

The present invention also relates to a method of preparing crystalline salts of (6R,S)-, (6S)- and (6R)-tetrahydrofolic acid, which is characterized in that the corresponding salt of tetrahydrofolic acid is crystallised. In this respect, crystallization of the tetrahydrofolic acid salt is preferably effected from a polar medium at a pH between 7 and 10.

Substances which are primarily suitable as the polar medium are water or a mixture of water and an organic solvent which is miscible with water, such as water-soluble alcohols, e.g., methanol, ethanol, n-propanol, isopropanol, ethylene glycol, a low molecular weight aliphatic, water-soluble carboxylic acid, e.g., formic acid, acetic acid or lactic acid, or water-soluble amides, e.g., formamide, dimethylformamide, dimethylacetamide, 1-methylpyrrolidone, 2-methylpyrrolidone or 2-piperidinone. There are no particular restrictions as regards the type of solvent used and the mixture ratio, since crystalline tetrahydrofolic acid salts generally have lower solubilities than the corresponding amorphous forms.

Crystallization is preferably effected at elevated temperature, particularly between 50° C. and 90° C., or from dilute solutions, particularly between 1% and 10%.

The crystallization of (6S)-, (6R)- and (6R,S)-tetrahydrofolic acid salts occurs spontaneously or is effected by seeding with the corresponding crystalline tetrahydrofolic acid salt.

Amorphous or crystalline, pure (6S)- or (6R)-tetrahydrofolic acid is preferably suitable as the starting material for crystallization. Racemic (6R,S)-tetrahydrofolic acid can also be used, however, as can enriched (6S)- or (6R)-tetrahydrofolic acid. Suitable starting materials here include both isolated solids, such as (6R,S)-tetrahydrofolic acid, (6S)-tetrahydrofolic acid-sulphuric acid and sulphonic acid addition salts prepared according to EP-495 204 for example, and also tetrahydrofolic acid which is prepared in situ from folic acid by catalytic hydrogenation or by borohydride reduction.

Due to the use of amorphous or partially crystalline, optically pure tetrahydrofolic acid or salts thereof as the starting material for the crystallization, salts of a purity which has hitherto not been achieved (>98%) and with a stability which has likewise never been achieved hitherto are obtained by the method described.

The present invention also relates to the use of crystalline (6S)-, (6R)- and/or (6R,S)-tetrahydrofolic acid salts as an ingredient for the production of drugs or for the preparation of other tetrahydrofolic acid derivatives, since crystalline (6S)-, (6R)- and (6R,S)-tetrahydrofolic acid salts maintain a very good quality, which is constant over time practically without restriction, due to their excellent stability in solid form. The invention further relates to pharmaceutical preparations containing crystalline (6S)-, (6R)- and/or (6R,S)-tetrahydrofolic acid salts. The pharmaceutical preparation is produced by known methods, such as freeze-drying for example. The solubility of the crystalline tetrahydrofolic acid salts in water at 20° C. is less than 1 mg/ml. Application is effected analogously to the application of known substances from the field of tetrahydrofolates, such as 5-formyl-5,6,7,8-tetrahydrofolic acid for example.

Furthermore, the present invention relates to a method of separating the magnesium salt of (6R,S)-tetrahydrofolic acid into the two diastereoisomers, namely the magnesium salts of (6S)- and (6R)-tetrahydrofolic acid, by fractional crystallization. This method is very simple and efficient. Even on the first crystallization of a crude racemic magnesium salt of (6R,S)-tetrahydrofolic acid, a crystalline magnesium salt of (6R)-tetrahydrofolic acid with a (6R)- fraction greater than 95% is obtained with yields of enantiomer greater than 50%. Crystalline magnesium salts of (6S)- and (6R)-tetrahydrofolic acid of higher isomeric purity can be obtained by further crystallizations under analogous conditions.

EXAMPLES TO ILLUSTRATE THE INVENTION

The contents of tetrahydrofolic acid salt and the fractions of isomers given in the examples were determined by HPLC in each case.

Example 1

(Stabilities)

In order to determine the stability of crystalline (6S)- and (6R)-tetrahydrofolic acid salts, the substances were stored, together with comparative samples, at 25° C. and 60% relative humidity under nitrogen, or at 4° C. in air. The remaining content of tetrahydrofolic acid salt was measured at periodic intervals and is given compared with the initial value.

Example 3

[TE 1423]

8.2 g (6R,S)-tetrahydrofolic acid were slurried under nitrogen in 100 ml water containing 1 g thioglycerol, the pH was adjusted to 3.3 with 30% aqueous sodium hydroxide solution, and the slurry was treated with a solution of 3.8 g calcium chloride in 4 g water. The resulting solution had a pH of 9.3. After stirring for 20 hours at room temperature, the resulting suspension, which had a pH of 10.0, was filtered under suction and the residue was washed with a little water.

After drying, 7.7 g of a slightly reddish, crystalline calcium salt of (6R,S)-tetrahydrofolic acid was obtained, which had a (6S)- fraction of 51.1% and a content amounting to 96%.

Example 4

[TE 1418]

28.6g (6R,S)-tetrahydrofolic acid were slurried under nitrogen in 114 ml water, the pH was adjusted to 7.5 with 30% aqueous sodium hydroxide solution, and the slurry was treated with a solution of 48.5 g calcium chloride in 500 ml water. The resulting rubber-like mass was heated to 90° C. After stirring for 1 hour, a bright yellow suspension was obtained, which was filtered hot under suction and washed with a little water.

After drying, 17.3 g of a beige, crystalline calcium salt of (6R,S)-tetrahydrofolic acid was obtained, which had a (6S)- fraction of 50.9% and a content amounting to 94%.

Example 5

[Am 593]

4.0 g (6R,S)-tetrahydrofolic acid were slurried under nitrogen in 40 ml water containing 0.4 g thioglycerol, the pH

|  |  | \multicolumn{6}{c}{Exposure time in months} |
| --- | --- | --- | --- | --- | --- | --- | --- |
|  |  | 0 | ½ | 1 | 2 | 6 | 9 |
| Crystaline Ca salt of | 25° C., 60%, $N_2$ | 100% | 98.5% | 97.2% | 96.8% | 97.7% | 97.7% |
| (6S)-tetrahydrofolic acid | 4° C., air | 100% | 95.5% | 92.4% | 89.2% | 82.3% | 76.0% |
| Crystalline Ca salt of | 25° C., 60%, $N_2$ | 100% | 97.8% | 96.1% | 98.0% | 97.1% | 96.8% |
| (6R)-tetrahydrofolic acid | 4° C., air | 100% | 85.9% | 79.0% | 73.0% | 69.3% | 69.2% |
| Crystalline Ca salt of | 25° C., 60%, $N_2$ | 100% | 99.3% | 98.0% | 99.0% | 97.8% | 98.7% |
| (6R,S)-tetrahydrofolic acid | 4° C., air | 100% | 96.5% | 94.2% | 89.0% | 86.6% | 86.2% |

Crystalline tetrahydrofolic acid salts were still very light in color even after a longer time of exposure. In contrast, amorphous samples rapidly became very strongly discolored.

After an exposure time of one month at 4° C. in air, the amorphous calcium salt of (6R,S)-tetrahydrofolic acid had a content which was 8% less than that of the crystalline calcium salt of (6R,S)-tetrahydrofolic acid.

Example 2

(X-ray Powder Spectra)

In order to characterize the structural properties (crystallinity) of the crystalline tetrahydrofolic acid salts, the X-ray powder spectra (diffraction spectra) of these substances were recorded.

Crystalline (6S)-, (6R)- and (6R,S)-tetrahydrofolic acid salts gave spectra of good resolution, and with sharp bands and a low background. The spectra indicated high crystalline contents.

was adjusted to 8.5 with 30% aqueous sodium hydroxide solution, and the slurry was treated with 2.0 g calcium acetate at 50° C. The beige product which slowly crystallized out from the resulting solution was filtered off under suction and the residue was washed with water.

After drying, 3.64 g of the crystalline calcium salt of (6R,S)-tetrahydrofolic acid was obtained, which had a (6S)- fraction of 50.5% and a content amounting to 94.6% (as the salt, with respect to the dry substance). The calcium content amounted to 1.12 equivalents.

Example 6

[Am 592]

12.0 g (6S)-tetrahydrofolic acid were slurried under nitrogen in 60 ml water containing 0.6 g thioglycerol, the pH was adjusted to 7.5 with 50% aqueous sodium hydroxide solution, and the slurry was treated at 85° C. with a solution of 22.5 g calcium chloride in 20 ml water. After stirring for 2 hours at 85° C., the product which crystallized out was filtered off under suction and washed with water.

After drying, 12.9 g of the crystalline calcium salt of (6S)-tetrahydrofolic acid was obtained, which had a (6S)-fraction of 99.9% and a content amounting to 96.8%. The solubility in water at 50° C. and at a pH of 6 of the product thus obtained was 0.12%.

Example 7

[Am 602]

By using 12.0 g (6R)-tetrahydrofolic acid and analogous treatment to that described in Example 6, 13.8 g of the crystalline calcium salt of (6R)-tetrahydrofolic acid were obtained which had a (6R)- fraction of 99.0% and a content amounting to 93%. The solubility in water at 50° C. and at a pH of 6 of the product thus obtained was 0.07%.

Example 8

[Am 482]

40.0 g (6S)-tetrahydrofolic acid were slurried under nitrogen in 160 ml water, and the pH was adjusted to 9.8 with 25% ammonia solution at 0–5° C. 34 g magnesium chloride in 34 ml water were added to the resulting solution. After adjusting the pH to 7.0 and adding 200 ml ethanol, the beige product which crystallized out was filtered off under suction and washed with ethanol/water.

After drying, 37.0 g of the crystalline magnesium salt of (6S)-tetrahydrofolic acid were obtained, which had a (6S)-fraction of 99.4% and a content amounting to 91.7%.

Example 9

[Am 583]

40.0 g (6R)-tetrahydrofolic acid were slurried under nitrogen in 400 ml water containing 4 g thioglycerol, and treated with 6.0 g magnesium hydroxide and 60.0 g magnesium acetate. The pH was adjusted to 9.0 at 50° C. with 25% ammonia solution. After cooling to 20° C., a gel-like mass was obtained which transformed into a fluid suspension on heating to 35° C. The suspension was filtered under suction at 35° C. and washed with water.

After drying, 18.0 g of the crystalline magnesium salt of (6R)-tetrahydrofolic acid were obtained, which had a (6R)-fraction of 99.4% and a content amounting to 92.0%.

Example 10

[Am 590]

20.0 g (6R,S)-tetrahydrofolic acid were slurried under nitrogen in 200 ml water containing 2 g thioglycerol, treated with 2.7 g magnesium hydroxide and heated to 50° C. After adding 30 g magnesium acetate, the pH was adjusted to 7.3 with 25% ammonia solution, and the solution was cooled to 20° C. and stirred overnight. The suspension obtained was filtered off under suction and washed with water.

After drying, 5.0 g of the crystalline magnesium salt of (6R)-tetrahydrofolic acid were obtained, which had a (6R)-fraction of 94.8% and a content amounting to 97.1%.

Example 11

[Am 506]

28.0 g (6R,S)-tetrahydrofolic acid were slurried under nitrogen in 110 ml water and 75 ml methanol containing 18 g thioglycerol, treated with 9.5 g magnesium hydroxide and the pH was adjusted to 9.3 at 50° C. with 25% ammonia solution. The fine suspension obtained after cooling to −5° C. was filtered off under suction and washed with a cold methanol/water mixture.

After drying, 10.5 g of the crystalline magnesium salt of (6R,S)-tetrahydrofolic acid were obtained, which had a (6S)-fraction of 49.5% and a content amounting to 95.9%.

Example 12

[Am 497]

4.0 g (6R,S)-tetrahydrofolic acid were slurried under nitrogen in 16 ml water, the pH was adjusted to 9.7 with 25% ammonia solution and the slurry was treated with 3.2 g magnesium chloride in 3.2 ml water. The resulting clear solution was introduced into 200 ml ethanol. After stirring for 2 hours, the light yellow suspension obtained was filtered under suction at 5° C. and washed with a cold ethanol/water mixture.

After drying, 4.5 g of the crystalline magnesium salt of (6R,S)-tetrahydrofolic acid were obtained, which had a (6S)-fraction of 49.3% and a content amounting to 90.3%.

The entire disclosures of all applications, patents and publications, cited above and below, and of corresponding application Swiss Appln. No. 03145/95, filed Nov. 7, 1995, are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A crystalline calcium salt of (6R,S)-, (6S)-, (6R)-tetrahydrofolic acid or combinations thereof.

2. A crystalline magnesium salt of (6R,S)-, (6S)-, (6R)-tetrahydrofolic acid or combinations thereof.

3. A method of preparing a crystalline calcium or magnesium salt of (6R,S)-, (6S)- and/or ((6R)-tetrahydrofolic acid, characterized in that a Ca or Mg salt of (6R,S)-, (6R)- or (6S)-tetrahydrofolic acid is crystallized in a polar medium at a pH between 7 and 10.

4. A method according to claim 3, characterized in that crystallization is effected at elevated temperature and/or from dilute solutions.

5. A method according to claim 4, characterized in that crystallization is effected in water or in a mixture of water and an organic solvent which is miscible with water.

6. A method according to claim 5, characterized in that acetic acid or a low molecular weight organic alcohol is used as the solvent miscible with water.

7. A method of using a crystalline calcium or magnesium salt of (6R,S)-, (6S)- or (6R)-tetrahydrofolic acid, which comprises incorporating said (6R,S)-, (6S)- or (6R)-tetrahydrofolic acid as an ingredient for the production of drugs.

8. A pharmaceutical preparation containing a crystalline calcium or magnesium salt of (6R,S)-, (6S)- or (6R)-tetrahydrofolic acid.

9. A method of preparing a crystalline calcium or magnesium salt of (6R,S)-, (6S)- and/or ((6R)-tetrahydrofolic acid, characterized in that (6R,S)-, (6R)- or (6S)-tetrahydrofolic acid is crystallized in a polar medium at a pH between 7 and 10.

* * * * *